United States Patent
Harris et al.

(10) Patent No.: US 8,112,159 B2
(45) Date of Patent: Feb. 7, 2012

(54) KIT FOR IMPLANTATION OF THERAPY ELEMENTS

(75) Inventors: Charmaine K. Harris, Woodbury, MN (US); Shahn S. Sage, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1275 days.

(21) Appl. No.: 10/958,210

(22) Filed: Oct. 4, 2004

(65) Prior Publication Data
US 2005/0107861 A1  May 19, 2005

Related U.S. Application Data

(60) Provisional application No. 60/508,389, filed on Oct. 3, 2003.

(51) Int. Cl.
*A61N 1/05* (2006.01)
(52) U.S. Cl. .................................. 607/116; 607/117
(58) Field of Classification Search ............. 607/116, 607/117; 606/185
See application file for complete search history.

(56) References Cited

U.S. PATENT DOCUMENTS

| | | | |
|---|---|---|---|
| 4,538,624 A | 9/1985 | Tarjan | |
| 4,808,157 A | 2/1989 | Coombs | |
| 5,205,828 A * | 4/1993 | Kedem | 604/158 |
| 5,255,691 A | 10/1993 | Otten | |
| 5,417,719 A * | 5/1995 | Hull et al. | 607/46 |
| 6,192,280 B1 * | 2/2001 | Sommer et al. | 607/122 |
| 6,205,361 B1 * | 3/2001 | Kuzma et al. | 607/116 |
| 6,309,401 B1 * | 10/2001 | Redko et al. | 606/185 |
| 6,553,264 B2 | 4/2003 | Redko et al. | |
| 6,587,733 B1 | 7/2003 | Cross, Jr. et al. | |
| 6,622,048 B1 * | 9/2003 | Mann et al. | 607/46 |
| 2002/0062143 A1 * | 5/2002 | Baudino et al. | 607/116 |
| 2003/0028147 A1 | 2/2003 | Aves et al. | |

FOREIGN PATENT DOCUMENTS

| | | |
|---|---|---|
| FR | 2688407 A | 9/1993 |
| FR | 2688407 A1 * | 9/1993 |
| WO | WO93/17737 | 9/1993 |
| WO | EP 1048270 A1 | 11/2000 |
| WO | EP 1048271 A2 | 11/2000 |

OTHER PUBLICATIONS

Translation of FR 2688407.* E. M. Delhaas "Extardural and subarachnoid catherterization using the Seldinger technique." British Journal of Anaesthesia. 1996; 76: 149-150.*
International Preliminary Report on Patentability, dated Oct. 28, 2005 for International Patent Application PCT/US2004/032540, filed Oct. 4, 2004 (10 pgs.).
International Search Report for Patent Application No. PCT/US2004/032540, Date Published: Apr. 14, 2005, (13 pgs.).

* cited by examiner

Primary Examiner — Eric D. Bertram
(74) Attorney, Agent, or Firm — Shumaker & Sieffert, P.A.

(57) ABSTRACT

This disclosure describes a kit to facilitate implantation of therapy elements into a patient, and techniques for percutaneously inserting therapy elements into a patient. In particular, embodiments of the invention are directed to techniques for percutaneously inserting two or more therapy elements into a patient via a single needle. In one embodiment, the invention is directed to a kit to facilitate implantation of therapy elements into a patient. The kit comprises a needle defining a lumen a first therapy element sized to pass through the lumen, and a second therapy element sized to pass through the lumen. The lumen is sized to receive both of the first and second therapy elements simultaneously. The first and second therapy elements are separate and not attached to one another such that distal ends of the first and second therapy elements can be positioned to provide therapy in distinct locations of the patient.

10 Claims, 5 Drawing Sheets

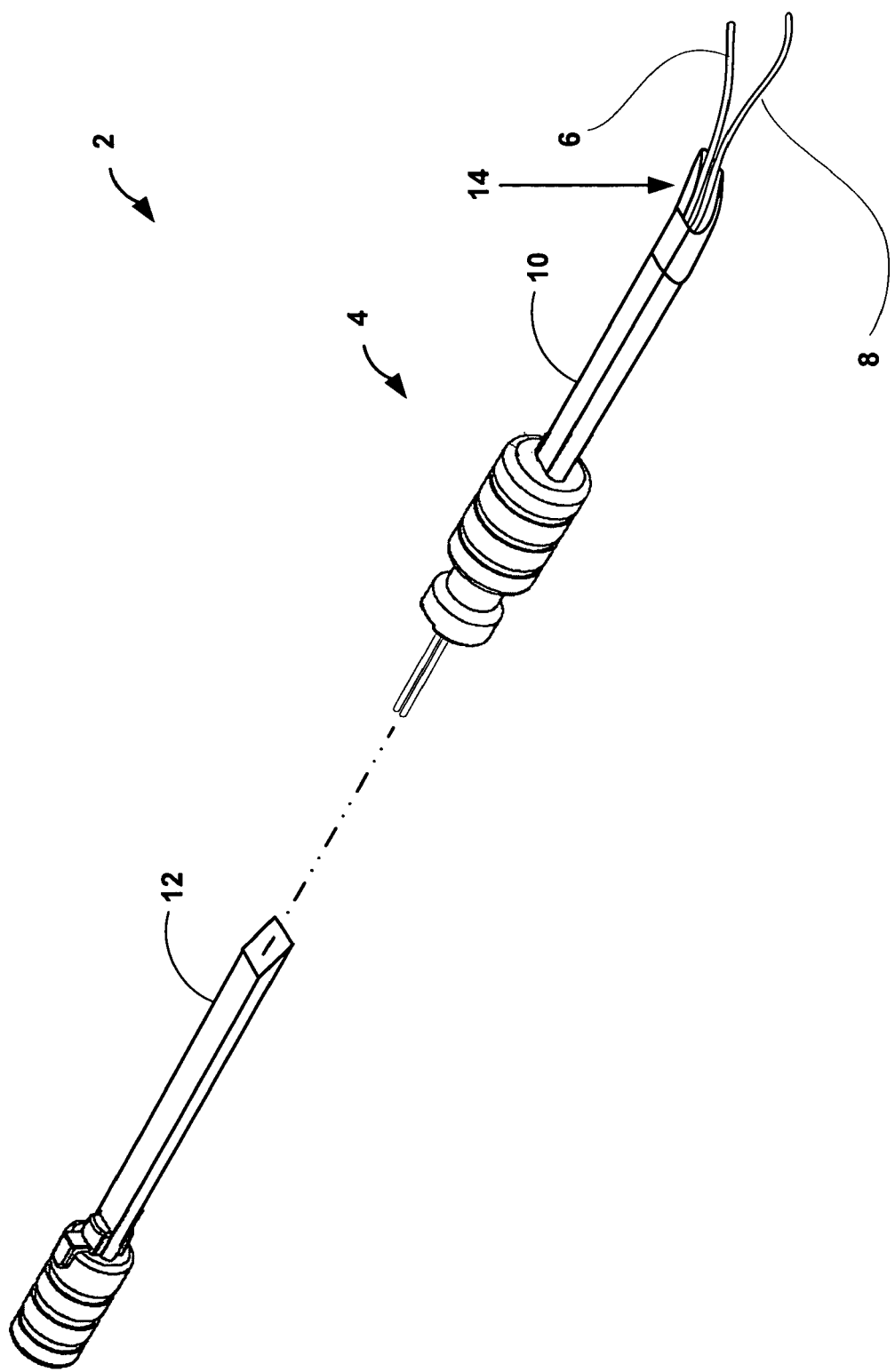

KIT FOR IMPLANTATION OF THERAPY ELEMENTS

This application claims the benefit of U.S. Provisional Application Ser. No. 60/508,389, filed Oct. 3, 2003, the entire content of which is incorporated herein by reference.

TECHNICAL FIELD

The invention relates to percutaneously implantable therapy elements such as percutaneous leads and catheters, more particularly, to introducers to facilitate implantation of such therapy elements.

BACKGROUND

Therapy elements such as percutaneous leads and catheters can be implanted through the skin to facilitate the delivery of stimulation therapy or drug therapy to patients. Neurostimulation and drug therapy may be used to treat a variety of symptoms or conditions such as chronic pain, movement disorders, pelvic floor disorders, Parkinson's disease, spinal cord injury, incontinence, gastroparesis and a wide variety of other medical conditions.

A neurostimulation system includes a stimulation device that delivers neurostimulation therapy through the leads to implantation sites proximate the distal ends of the leads. The distal ends of the leads include one or more electrodes that are electrically coupled to the stimulation device via conductors that extend along the lead body. The stimulation therapy takes the form of electrical pulses delivered at the electrodes. Neurostimulation systems are commonly used to deliver stimulation therapy to the spinal cord, pelvic nerves, stomach, or within the brain of a patient.

A drug therapy system delivers drug therapy in the form of therapeutic agents. In general, drug therapy systems include an implantable pump that delivers drug therapy via catheters having delivery regions located proximate to local therapy site within a patient.

Percutaneous leads and catheters are often preferred over surgically implanted leads and catheters because percutaneously implanted leads and catheters are implanted in a less invasive manner. For example, in order to implant percutaneous leads for spinal cord stimulation (SCS) an incision is made to ease the introduction of an introducer, such as a percutaneous needle. The needle is inserted through the incision and positioned to access the epidural space. The lead is then inserted through the needle and positioned to a desired location, e.g., within the epidural space. After the lead has been properly positioned, the needle is withdrawn and the lead is connected to a stimulation device. The stimulation device is typically implanted just below the patient's skin.

SUMMARY

Embodiments of the invention are directed to a kits to facilitate implantation of therapy elements into a patient and techniques for percutaneously inserting two or more therapy elements into a patient. In particular, the invention is directed to techniques for percutaneously inserting two or more therapy elements into a patient via a single needle. The needle may be a paddle-shaped needle capable of simultaneously receiving the two or more therapy elements. The needle defines a lumen sized to receive the two or more therapy elements simultaneously. The first therapy element is inserted through the lumen of the needle to position a distal end of the first therapy element at a first implant location. The second therapy element is then inserted through the lumen of the needle to position a distal end of the second therapy element at a second implant location.

The first and second therapy elements may comprise electrical leads that provide neurostimulation, catheters that provide drug therapy, or any combination of both electrical leads and catheters. In any case, the first and second therapy elements may be placed independently at the first and second implant locations. In an embodiment, the first and second therapy elements are separate and not attached to each other. Accordingly, the first and second therapy elements may be positioned to deliver therapy at distinct locations within the patient, e.g. a region proximate to the right side of the spine of a patient, and a region proximate to the left side of the spine. The use of a single needle can make the implantation of two or more therapy elements less invasive than techniques that require separate needles to implant separate therapy elements.

In one embodiment, the invention is directed to a kit to facilitate implantation of therapy elements into a patient. The kit comprises a needle defining a lumen, a first therapy element sized to pass through the lumen, and a second therapy element sized to pass through the lumen. The lumen is sized to receive both of the first and second therapy elements simultaneously. The first and second therapy elements may be moved independently within the lumen. For example, the therapy elements may be separate and not attached to one another such that distal ends of the first and second therapy elements can be positioned to provide therapy in distinct locations of the patient.

In another embodiment, the invention provides a method comprising inserting a needle into a patient, the needle defining a lumen sized to receive two or more therapy elements simultaneously, inserting a first therapy element through the lumen of the needle to position a distal end of the first therapy element at a first implant location, and inserting a second therapy element through the lumen of the needle to position the distal end of the second therapy element at a second implant location.

Various embodiments of the invention may be capable of providing one or more advantages. For example, embodiments of the invention may simplify and improve techniques for percutaneously inserting two or more therapy elements into a patient. Again, the described techniques can be used to implant electrical leads that provide neurostimulation therapy, catheters that provide drug therapy, or any combination of electrical leads and catheters into an epidural region proximate to the spine of the patient. Importantly, the techniques can facilitate such implantation in a less invasive fashion than conventional kits and techniques. The different therapy elements may be independently placed. As an example, the therapy elements may be separate and not attached to each other and, therefore, may be positioned to deliver therapy at distinct locations within the patient. In accordance with an embodiment of the invention, however, only a single needlestick is required, thus reducing the risk of trauma that may be caused by an additional needlestick. In one example, the first therapy element may be positioned in an epidural region proximate to the left side of the spine to relieve lower back pain while the second therapy element may be positioned in an epidural region proximate to the right side of the spine to relieve leg pain.

Unlike some conventional techniques that make use of two leads that are bonded together, the described techniques make use of two or more therapy elements that are independently moveable. For example, the therapy elements may be separate and not attached to each other. As a result, the risk of therapy elements shorting together may be reduced relative to conventional bonded elements. Additionally, a first implanted therapy element may be used as a guide to improve the positioning of a second therapy element and reduce the risk of additional trauma to the patient and/or damage to the therapy elements.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 1 is a diagram illustrating a kit to facilitate implantation of therapy elements into a patient.

DETAILED DESCRIPTION

Figure 2A:
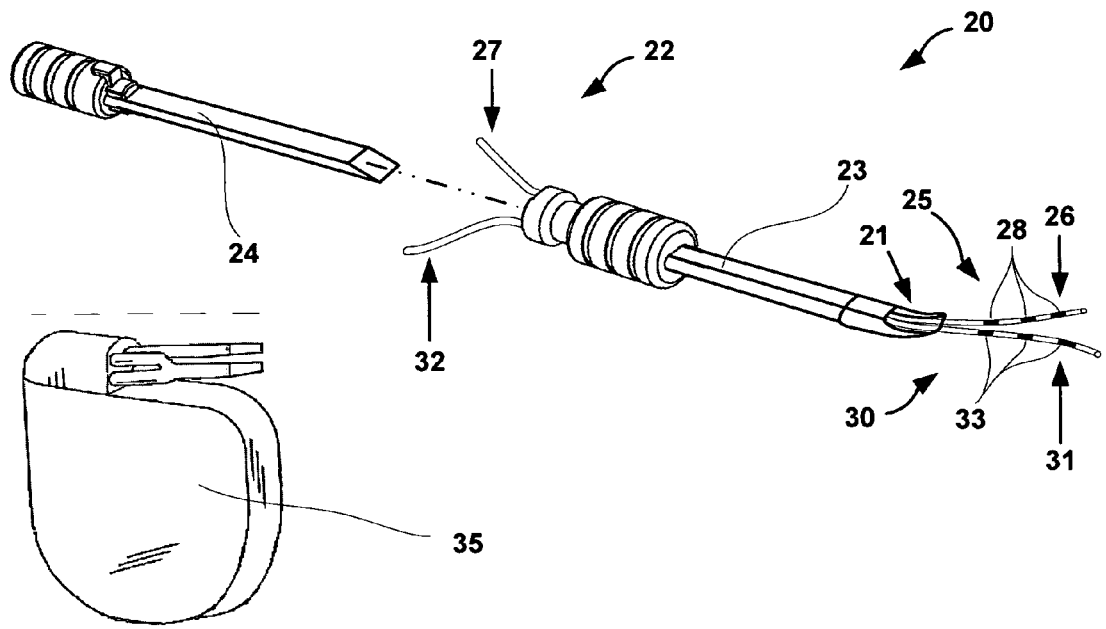
FIGS. 2A, 2B are diagrams illustrating a kit to facilitate implantation of two electrical leads of a neurostimulation system into a patient.

FIG. 1 is a diagram illustrating therapy element implantation kit 2, which includes components for percutaneously implanting two or more therapy elements in a patient. In the illustrated embodiment, kit 2 includes a first therapy element 6 and a second therapy element 8 that can be percutaneously implanted into a patient through a needle 4. First and second therapy elements 6, 8 are separate and not attached to one another. In this manner, first and second therapy elements 6, 8 may be inserted in needle 4, and independently positioned to deliver therapy at distinct locations within the patient using a single needlestick. For example, therapy elements 6, 8 may be implanted on different sides of a patient's spin for spinal cord therapy. The invention may also facilitate implantation of two or more therapy elements in other therapeutically distinct locations within a patent. The elements in kit 2 are not necessarily shown to scale in FIG. 1.

In general, needle 4 is inserted into a patient through an incision made by a physician. The physician may perform a loss of resistance technique to properly position needle 4, e.g., in the epidural space proximate to a spine of the patient. More specifically, first therapy element 6 may be inserted into the patient through a lumen of needle 4 to a first implant location, e.g. an epidural region proximate to one side of the spine of the patient. Second therapy element 8 is then inserted through the lumen of needle 4 to a second implant location, e.g., an epidural region proximate to another side of the spine of the patient. Importantly, second therapy element 8 is inserted through needle 4 while first therapy element 6 is still disposed within needle 4. In other words, first and second therapy elements 6, 8 are capable of being moved independently within the lumen.

First therapy element 6 and second therapy elements 8 may be separate and not attached to one another, which provides freedom to the physical in placement of the elements. In some embodiments, the physician may advance needle 4 after positioning first therapy element 6 to access a second implant location that is substantially different than the first implant location, e.g. an intrathecal region proximate to the spine of the patient. Once first and second therapy elements 6, 8 are properly implanted, needle 4 is withdrawn from the patient and first and second therapy elements 6, 8 are attached to a corresponding therapy device.

Needle 4 defines a lumen sized to receive both the first and second therapy elements 6, 8 simultaneously. Needle 4 may include a cannula 10 which defines the lumen and a needle stylet 12. The lumen may be between approximately 14 gauge and 18 gauge to allow cannula 10 to receive first and second therapy elements 6, 8 simultaneously as well as receive needle stylet 12. The lumen has an opening 14 and defines a substantially oblong cross section wherein the width of the lumen is greater than the height. In some embodiments, the width of the lumen may be approximately 0.171 inches (0.434 centimeters) and the height may be approximately 0.065 inches (0.164 centimeters). In any case, opening 14 is also sized to receive first and second therapy elements 6, 8 simultaneously. Needle stylet 12 is sized to substantially fill cannula 10 to prevent coring in the tissue of the patient when needle 4 is inserted into the patient. Generally, needle 4 defines an opening and lumen suitable for receiving two or more therapy elements simultaneously. European Patent No. 1048270A1, U.S. Pat. No. 6,309,401, and 6,553,264 describe suitable needles and are incorporated by reference herein. In some instances, needle 4 may take the form of a modified Tuohy needle which has an opening that is angled, e.g. approximately 45 degrees so that an instrument passing through the needle exits through the needle at an angle. Needle 4 may be made of any material suitable for positioning therapy elements. For example, needle 4 may be made from stainless steel and/or plastic.

Generally, kit 2 may include including two or more therapy elements. Each therapy element may comprise an electrical lead that provides neurostimulation, a catheter that provides drug therapy, or another therapy element shaped similar to catheters or leads. Kit 2 may include a two electrical leads, two catheters, and an electrical lead and a catheter, or possibly three or more leads and/or catheters. In other words, a third therapy element may also be included in kit 2, and the therapy elements included in kit 2 may comprise any combination of electrical leads and catheters.

In embodiments in which electrical stimulation is desired, kit 2 includes at least one electrical lead that may be part of a neurostimulation system including a neurostimulator such as an Itrel II® Model 7424 or an Itrel 3® Model 7425, both of which are commercially available from Medtronic, Inc. of Minneapolis, Minn. The invention is not limited to use with Itrel Model neurostimulators, however, and may be adapted for use with other models of implantable neurostimulators. Alternatively, the electrical lead may be part of a neurological monitoring system including a neurological monitor such as a Medtronic Neurodiagnostics Keypoint monitoring system which is commercially available from Medtronic, Inc. of Minneapolis, Minn. In any case, the electrical lead may comprises a proximal end, a distal end, and a lead body. As used herein the term "proximal end" refers to the region of the therapy element that connects to the implantable device, but is not limited to the proximal-most tip of the element. Similarly, the term "distal end" refers to the region of the implanted device proximate the distal most tip, but may include some portion of the element proximate the tip. The distal portion of a lead, for example, may include the electrodes of the lead, even if such electrodes are disposed some distance from the distal most tip. The distal portion of a catheter may define the delivery region for delivery of drugs or agents.

The proximal end of an electrical lead includes at least one electrical connector (also known as an electrical terminal) and is coupled to a neurostimulator/neurological monitor. The stimulation pulses generated by the neurostimulator are transmitted from the neurostimulator through one or more conductors in the lead body to the distal end of the electrical lead. The distal end of the electrical lead includes at least one electrode that delivers neurostimulation to the targeted tissue of the patient, although the electrode may or may not be disposed on the distal-most tip of the lead. The lead body includes at least at least one conductor that electrically connects the electrical connector to the electrodes at the distal end. The electrical lead can be configured as a neurological stimulation lead, a neurological sensing lead, and a combination of both as a neurological stimulation and sensing lead.

In any event, once one or more leads have been percutaneously implanted, the leads can be attached to the neurostimulator, which is then typically implanted subcutaneously in the patient at a location selected by a physician. As an example, a physician may insert an electrical lead through needle 4 to an epidural region proximate to the spine of the patient, remove needle 4, and then attach the proximal end of the electrical lead to the neurostimulator, which is then implanted.

In embodiments that facilitate drug delivery, kit 2 includes at least one catheter that may be a part of an implantable drug pump system. In that case, the system may include an implantable drug pump that comprises a reservoir containing a drug. Examples of implantable pumps include a number of SynchroMed™ pumps manufactured by and commercially available from Medtronic Inc. The invention is not limited to use with SynchroMed™ pumps, however, and may be adapted for use with other models of implantable drug pumps. In any case, the catheter attaches to the implantable drug pump via the proximal end of the catheter and delivers drug therapy by dispensing a drug contained in the reservoir to a targeted location within the patient. A fluid comprising the drug therapy is delivered to the patient through one or more delivery regions of the catheter, typically located at the distal end of the catheter. The drug pump is typically implanted subcutaneously in the patient at a location selected by the physician, but the catheter may be implanted percutaneously at a location selected by the physician by inserting the catheter through needle 4. For example, a physician may insert a catheter through needle 4 to an epidural region proximate to the spine of the patient or a intrathecal region proximate the spine. After removing the needle, the physician can attach the proximate end of the catheter to the implantable drug pump.

In general, first and second therapy elements 6, 8, are inserted through the lumen of needle 4 such that the distal ends of first and second therapy elements 6, 8 are positioned to provide therapy in distinct locations of the patient. The distinct locations may be therapeutically distinct such that the different therapy elements 6, 8, provide different therapeutic effects. Importantly, first and second therapy elements 6, 8 are separate and not attached to each other, thereby allowing for distinct positioning and therapeutically distinct application of therapy. However, because both first and second therapy elements 6, 8 are inserted through needle 4 only a single needlestick is required and the risk of trauma that may be caused by an additional needlestick is eliminated. Furthermore, by using a single needlestick the risk of damaging an already inserted therapy element from an additional needlestick is eliminated.

The described invention may be advantageous when inserting and positioning a first therapy element followed by inserting and positioning a second therapy element because the first therapy element may be used as a guide when positioning the second therapy element. As a result, the risk of additional trauma to the patient and/or damage to the already inserted therapy element is further reduced. Moreover, because the therapy elements are separate and not attached to each other, risks of electrical lead shorting is also reduced. Therapy elements may be inserted very easily using a paramedian technique. In that case, the therapy elements are typically not positioned proximate to the midline of the spine of the patient. Midline positioning, however, could be used, if desired.

Positioning first and second therapy elements 6, 8 at distinct locations of the patient may be particularly desirable for treating bi-lateral pain of the patient. For example, first therapy element 6 may be an electrical lead having an electrode positioned at an epidural region proximate to the right lumbar area of the spine of the patient to treat leg pain, while second therapy element 8 may be an electrical lead having an electrode positioned at an epidural region proximate to the left thoracic area of the spine of the patient to treat lower back pain. In general, therapy elements may be selectively staggered to provide therapy to any epidural region proximate the spine of the patient. In a further example, first therapy element 6 may be a catheter having a delivery region positioned at an intrathecal region of the spine of the patient to deliver morphine, or another agent to treat chronic pain, while second therapy element 8 may be a catheter having a delivery region positioned at another intrathecal region of the spine of the patient to deliver agents to that region. Catheters could also be implanted in the epidural space in some applications. The agents delivered to the different regions may be the same or different. The same drug pump or distinct drug pumps may be used with the different catheters.

In yet another example, first therapy element 6 may be an electrical lead having an electrode positioned at an epidural region proximate to the midline of the spine of the patient to treat lower back pain while second therapy element 8 may be a catheter having a delivery region positioned at an intrathecal region of the spine of the patient to deliver morphine to treat chronic pain. Generally, first and second therapy elements 6, 8 may be positioned to deliver therapy to any epidural region proximate to the spine of the patient including the lumbar, thoracic, and cervical regions spine as well as along the midline, right side, or left side of the spine. Moreover, the invention is not limited to percutaneously implanting therapy elements within an epidural region proximate to the spine of a patient and may be used to percutaneously implant therapy elements, possibly for deep brain stimulation or any therapy system that makes use of percutaneously implanted therapy elements. Numerous other implantation locations where the invention may be used may become apparent in view of this disclosure. Two distinct implantation locations may allow for complementary therapy to be provided.

Figure 2B:
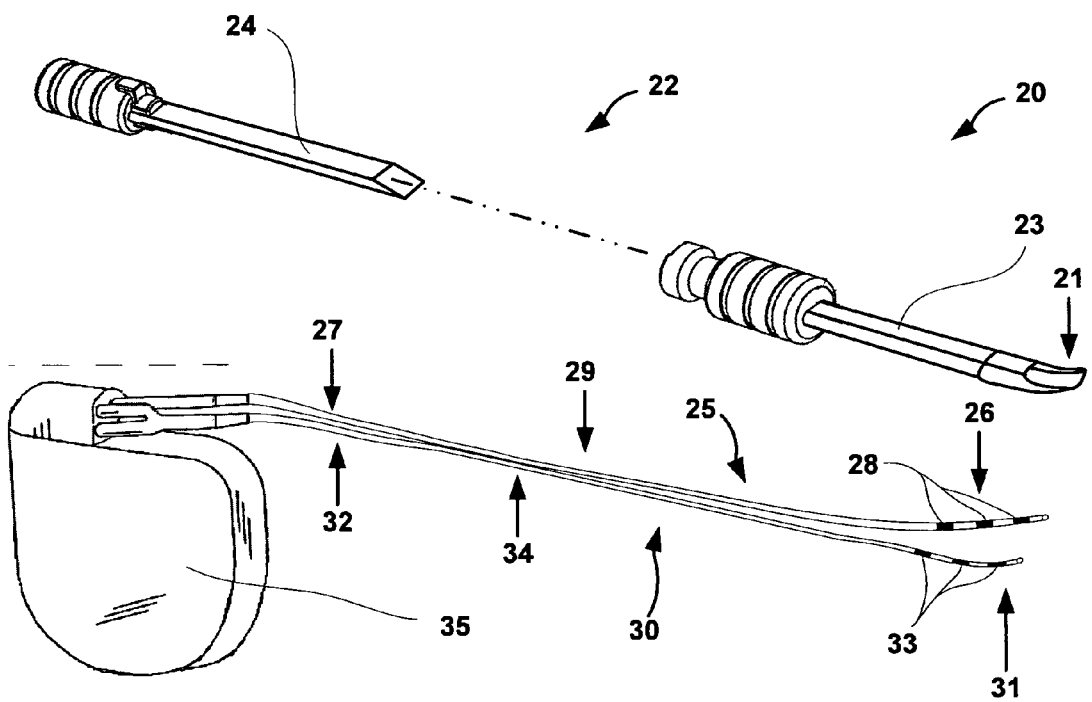

FIGS. 2A and 2B are diagrams illustrating therapy element implantation kit 20 that includes needle 22 and first and second electrical leads 25, 30, herein referred to as leads 25, 30, that attach to neurostimulator 35 to form a neurostimulation system. FIG. 2A illustrates kit 20 with leads 25, 30 disposed within needle 4 simultaneously. Leads 25, 30 may be implanted percutaneously within a patient and are not attached to neurostimulator 35 during such implantation. Accordingly, with needle 22 implanted within the patient, leads 25, 30 may be inserted separately and positioned at a first and a second implant location, respectively. Neurostimulator 35 may be implanted subcutaneously within the patient in a separate procedure either before or after lead implantation. Leads 25, 30 can be attached to neurostimulator 35 after being positioned within the patient.

FIG. 2B illustrates needle 22 separate from leads 25, 30 which are attached to neurostimulator 35. Needle 22 may be withdrawn from a patient once leads 25, 30 have been percutaneously implanted and properly positioned within the patient. After withdrawing needle 22, leads may be attached to neurostimulator 35 and the patient may receive neurostimulation therapy via leads 25, 30.

The elements in FIGS. 2A, 2B are not necessarily shown to scale. Leads 25, 30 are separate and not attached to one another. In this manner, leads 25, 30 may be inserted and positioned to deliver therapy at distinct locations within the patient using only needle 22 with a single needlestick. In general, the therapy elements are independently positionable. It may be possible, however, for therapy elements to be attached in a slideable fashion, while still allowing such elements to be independently positionable. The distal ends, however, generally remain unattached allowing the distal ends to be positioned in therapeutically distinct locations.

Needle 22 defines a lumen sized to receive leads 25, 30 simultaneously. Needle 22 may include a cannula 23 which defines the lumen and a needle stylet 24. The lumen may be between approximately 14 gauge and 18 gauge to allow cannula 23 to receive leads 25, 30 simultaneously as well as receive needle stylet 24. The lumen has an opening 21 having a substantially oblong cross section wherein the width of opening 21 is greater than the height. In some embodiments, the width of opening 21 may be approximately 0.171 inches (0.434 centimeters) and the height may be approximately 0.065 inches (0.165 centimeters). The lumen may have similar dimensions, or may be slightly smaller. In any case, opening 21 is sized to receive leads 25, 30 simultaneously. Needle stylet 24 is sized to substantially fill cannula 23 to prevent coring in the tissue of the patient when needle 22 is inserted into the patient. Generally, needle 22 may include any needle having an opening and lumen suitable for receiving two or more therapy elements simultaneously. Needle 22 may be made of any material suitable for positioning therapy elements. For example, needle 22 may be made from stainless steel and/or plastic.

After being implanted in a patient, leads 25, 30 are attached to neurostimulator 35 to define a neurostimulation system that may be used to treat conditions such as pain, movement disorders, pelvic floor disorders, and gastroparesis. In operation, neurostimulator 35 generates neurostimulation energy delivered to target locations within the patient via leads 25, 30. In particular neurostimulator 35 may be an implantable neurostimulator subcutaneously implanted in the patient at a location selected by a physician, while leads 25, 30 may be percutaneously inserted and positioned within the patient by the physician at distinct locations. For example, electrical lead 25 may be percutanesouly implanted in an epidural region proximate to the right side of the lumbar region of the spine of the patient while second electrical lead may be percutaneouslly implanted in an epidural region proximate to the left side of the thoracic region of the spine of the patient. Midline spinal implantation alternatively or additionally be used in some applications.

Neurostimulator 35 includes a housing, a power supply carried in the housing, and stimulation electronics coupled to the battery and to a connector block. Neurostimulator 35 may comprise an implantable neurostimulator such as an Itrel II® Model 7424 or an Itrel 3® Model 7425 or, alternatively, a neurological monitor such as a Medtronic Neurodiagnostics Keypoint monitoring system. Itrel II® Model 7424, Itrel 3® Model 7425 and the Medtronic Neurodiagnostics Keypoint monitoring system are commercially available from Medtronic, Inc. of Minneapolis, Minn. Again, the invention is not limited to use with Itrel Model neurostimulators or the Medtronic Neurodiagnostics keypoint monitoring system, however, and may be adapted for use with other models of neurostimulators and neurological monitoring systems.

Each of leads 25, 30 comprises a proximal end 27, 32, a distal end 26, 31, and a lead body 29, 34, respectively. Each of proximal ends 27, 32 includes at least one electrical connector that couples to neurostimulator 35. Each of distal ends 26, 31 includes at least one electrode. Leads 25, 30 are each shown in FIGS. 2A, 2B with three surface electrodes 28, 33, respectively, although any number of electrodes could be used. At least one conductor is included in each of lead body 29, 34 electrically connects the electrical connectors in proximal ends 27, 32 to electrodes 28, 33 in distal ends 26, 31. The conductor may comprise a conductive material, and may assume a variety of configurations. Conductor materials include, but are not limited to, MP35N, silver drawn filled tubing (Ag-DFT), platinum iridium alloys, platinum and the like. Conductor configurations may include stranded, braided or solid wire configured in a linear or helical coil arrangement. Additionally, the conductor contained in lead body 29, 34 may be electrically isolated by a polymer. The polymer may include, but is not limited to, ethylene tetrafluoroethylene (ETFE), polytetrafluoroethylene (PTFE), silicone rubber, and polyurethane or other such electrically insulating materials. Lead bodies 29, 34 may include an outer sheath composed of any of a variety of materials. Sheath materials may include, but are not limited to, silicone rubber, polyurethane, fluoropolymers and the like. Monolumen and multilumen tubings could also be used. The outer diameter of leads 25, 30 may be approximately 0.048 inches (0.122 centimeters) to approximately 0.055 inches (0.140 centimeters).

Again, kit 20 can provide advantages when percutaneously inserting and positioning leads 25, 30 through needle 22 using a single needlestick. For example, by inserting and positioning electrical lead 25 through needle 22, the physician may subsequently use electrical lead 25 as a guide when inserting electrical lead 30 through needle 22 and thus, reduce the risk of additional trauma to the patient and/or damage to the already inserted electrical lead 25. Furthermore, with leads 25, 30 being separate and are not attached to each other the risk of the electrical leads shorting together is reduced. Leads 25, 30 can be inserted very easily when using a paramedian technique, particularly if the leads 25, 30 are not required to be positioned in an epidural region proximate to the midline of the spine of the patient.

Positioning leads 25, 30 at distinct locations of the patient may be particularly desirable for treating multiple areas of pain of the patient. For example, electrical lead 25 may be an electrical lead having one or more electrodes positioned at an epidural region proximate to the right lumbar area of the spine of the patient to treat leg pain while electrical lead 30 may be an electrical lead having one or more electrodes positioned at an epidural region proximate to the left thoracic area of the spine of the patient to treat lower back pain. In general, the electrodes of leads 25, 30 may be selectively staggered to provide therapy to any epidural region proximate the spine of the patient. Moreover, the invention is not limited to percutaneously implanting electrical leads within an epidural region proximate to the spine of a patient and may be used to implant therapy elements for deep brain stimulation or other such therapy systems that require percutaneously implanted electrical leads. Catheters might also be used for deep brain drug therapy or other therapy systems that require percutaneously implanted catheters.

Figure 3A:
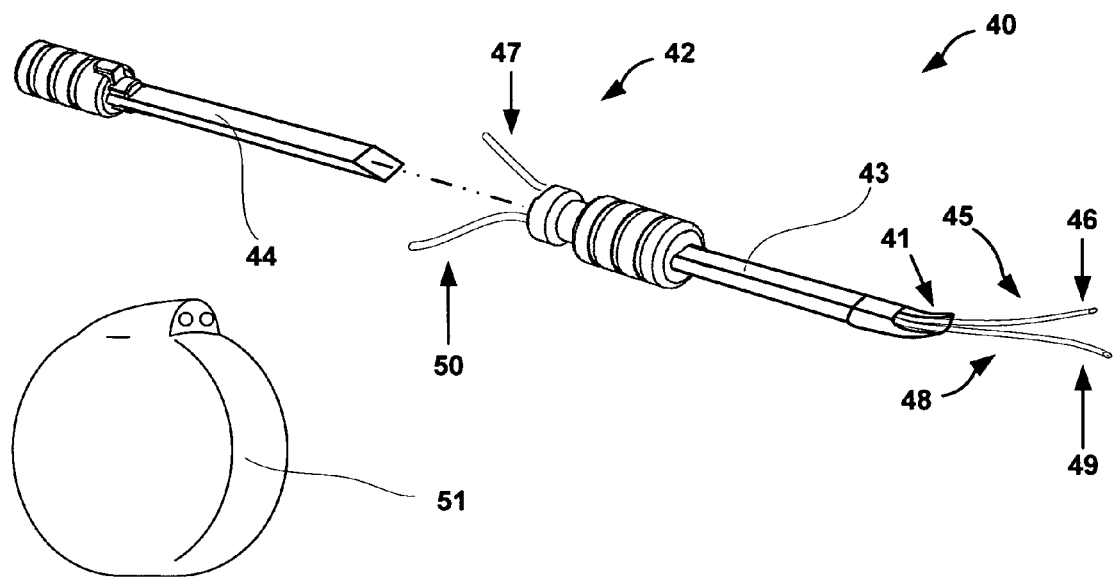
FIGS. 3A, 3B are diagrams illustrating a kit to facilitate implantation of two catheters of an implantable drug therapy system into a patient.
Figure 3B:
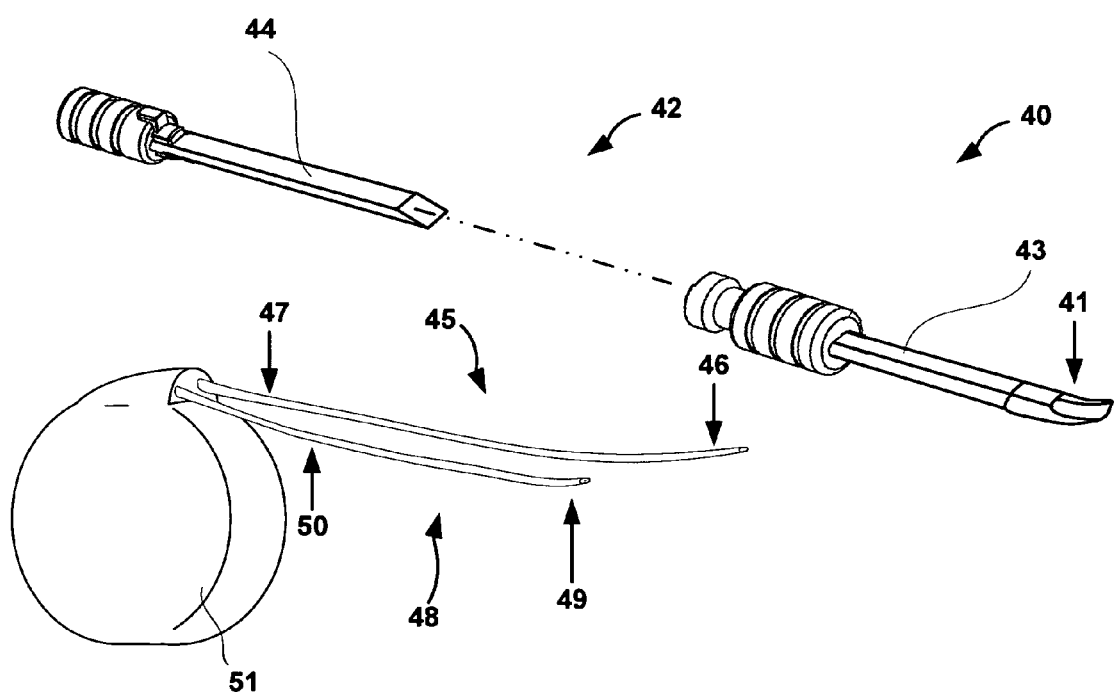

FIGS. 3A, 3B are diagrams illustrating therapy element implantation kit 40 that includes needle 42 and first and second catheters 45, 48, herein referred to as catheters 45, 48, that attach to drug pump 51 to form a drug therapy system. FIG. 3A illustrates kit 40 with catheters 45, 48 disposed within needle 42 simultaneously. Catheters 45, 48 may be implanted percutaneously within a patient and are not attached to drug pump 51 during the implantation. With needle 42 implanted within the patient, catheters 45, 48 may be inserted separately and positioned at a first and a second implant location, respectively. Drug pump 51 may be implanted subcutaneously within the patient through a separate procedure. Catheters 45, 48 may be attached to drug pump 51 after being positioned within the patient. Alternatively, different drug pumps may be used for the different catheters 45, 48.

FIG. 3B illustrates needle 42 separate from catheters 45, 48, which are attached to drug pump 51. Needle 42 may be withdrawn from the patient after catheters 45, 48 are percutaneously inserted and positioned within the patient. After withdrawing needle 42, catheters 45, 48 may be attached to drug pump 51 and the patient may receive drug therapy via catheters 45, 48.

The elements in FIGS. 3A, 3B are not necessarily shown to scale. Importantly, catheters 45, 48 are independently positionable. In one example, catheters 45, 48 are separate and not attached to one another. In this manner, catheters 45, 48 may be inserted and positioned to deliver therapy at distinct locations within the patient using only needle 22 with a single needlestick.

Needle 42 defines a lumen sized to receive catheters 45, 48 simultaneously. Needle 42 may include a cannula 43 which defines the lumen and a needle stylet 44. The lumen may be between approximately 14 gauge and 18 gauge to allow cannula 43 to receive catheters 45, 48 simultaneously as well as receive needle stylet 44. The lumen has an opening 41 having a substantially oblong cross section wherein the width of opening 41 is greater than the height. In some embodiments, the width of opening 41 may be approximately 0.171 inches (0.434 centimeters) and the height may be approximately 0.065 inches (0.165 centimeters). In any case, opening 41 is sized to receive catheters 45, 48 simultaneously. Needle stylet 44 is sized to substantially fill cannula 43 to prevent coring in the tissue of the patient when needle 42 is inserted into the patient. Needle 42 may be made of any material suitable for positioning therapy elements, such as stainless steel and/or plastic.

When implanted in a patient, catheters 45, 48 attached to drug pump 51 comprise a system that may be used to treat conditions such as chronic pain or other disorders. In operation, drug pump 51 delivers small dosages of a drug to target locations within the patient via catheters 45, 48. In particular drug pump 51 may be an implantable drug pump subcutaneously implanted in the patient at a location selected by a physician. Catheters 45, 48 may be percutaneously inserted and positioned within the patient by the physician such that delivery regions of catheters 45, 48 are located at distinct locations. Catheters 45, 48 can then be connected to drug pump 51.

In general, drug pump 51 includes a housing, a power supply carried in the housing, a reservoir that contains a drug, and electronics coupled to the battery and to a connector block. Examples of implantable pumps include a number of SynchroMed™ pumps manufactured by and commercially available from Medtronic Inc., although the invention is not limited to use with specific types or models of drug pumps.

In any case, catheters 45, 48 attach to the drug pump 51 via proximal end 47, 50 of catheters 45, 48, respectively. In general catheters 45, 48 may include any catheter suitable for percutaneous insertion. The outer diameter of catheters 45, 48 may be approximately 0.024 inches (0.061 centimeters) to approximately 0.060 inches (0.152 centimeters). Catheters 45, 48 deliver drug therapy by dispensing dosages of the drug contained in the reservoir of drug pump 51 to a targeted location within the patient via delivery regions, typically disposed on distal ends 46, 49. In one example, a physician may percutaneously insert catheter 45 through needle 42 to an intratehcal region proximate to one side of the spine of the patient to facilitate delivery of morphine to the cerebrospinal fluid (CSF) and percutaneously insert catheter 48 through needle 42 to an intrathecal region proximate to another side of the spine of the patient facilitate delivery of morphine to the CSF. Alternatively, different types of agents may be administered by the different catheters. After positioning catheters 45, 48, the physician may withdraw needle 42 and attach proximate ends 47, 50 of catheters 45, 48, respectively, to drug pump 51. Different drug pumps could also be used with the different catheters.

Figure 4A:
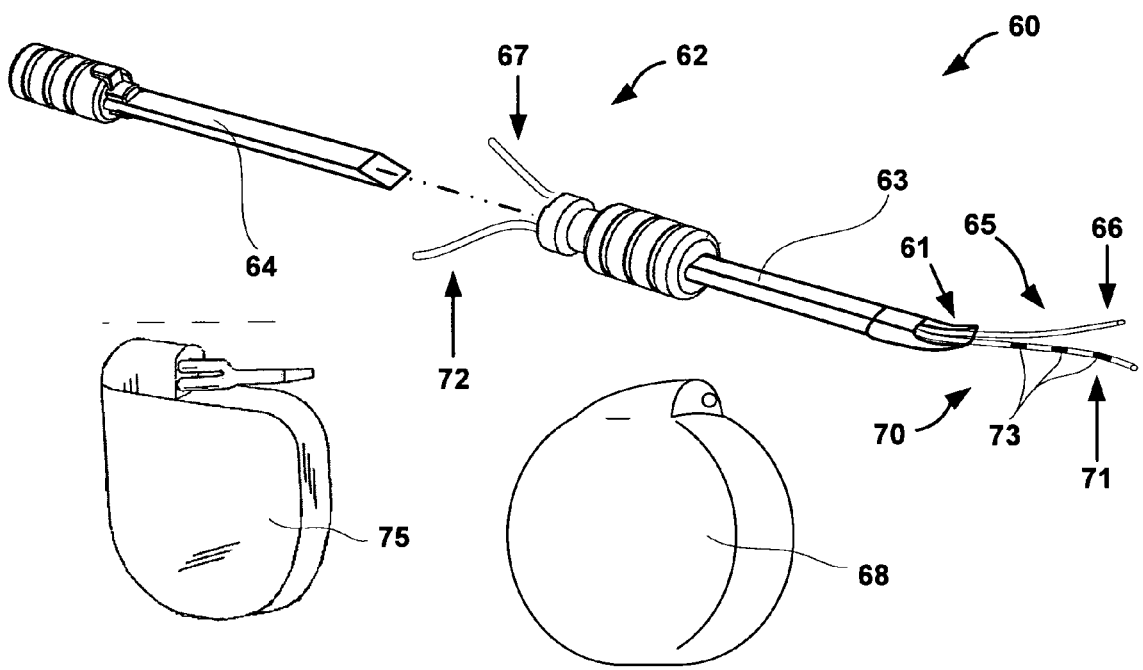
FIGS. 4A, 4B are diagrams illustrating a kit to facilitate implantation of an electrical lead of a neurostimulation system and a catheter of an implantable drug therapy system into a patient.
Figure 4B:
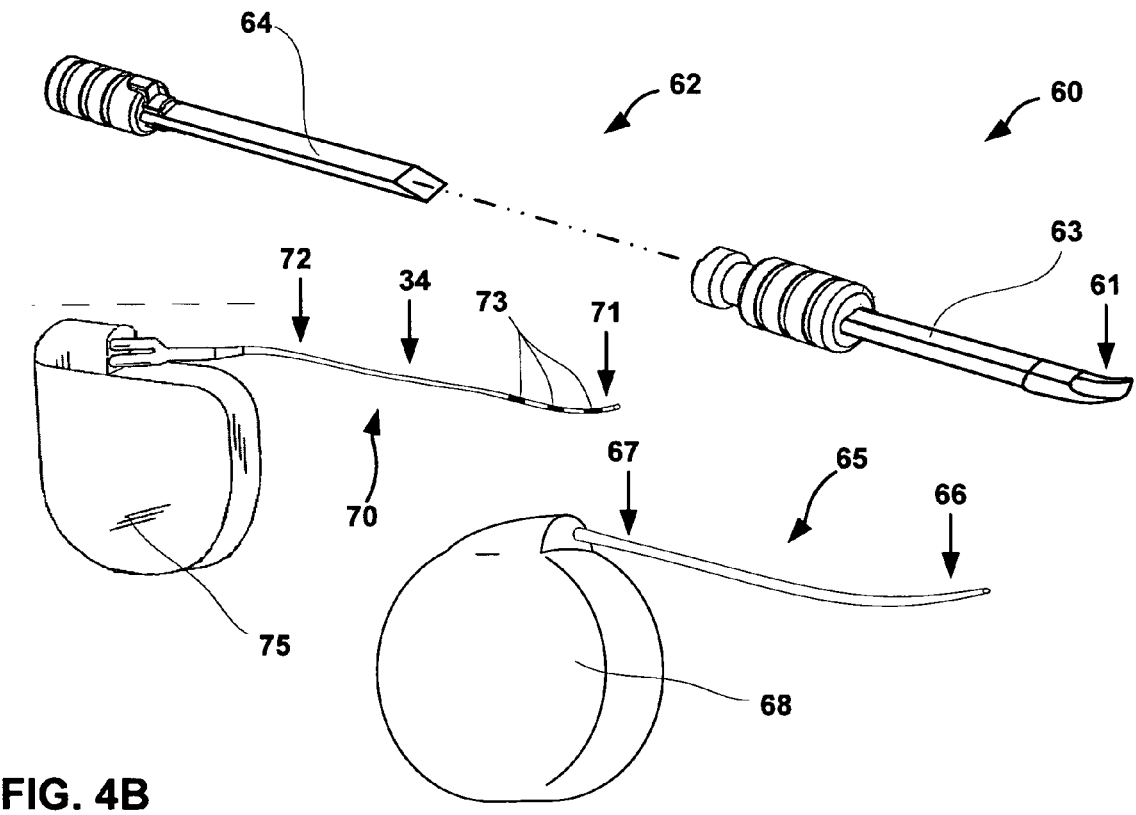

FIGS. 4A, 4B are diagrams illustrating therapy element kit 60 that includes needle 62, catheter 65 and electrical lead 70. Catheter 65 attaches to drug pump 68 to form a drug therapy system. Electrical lead 70 attaches to neurostimulator 75 to form a neurostimulation system. FIG. 4A illustrates kit 60 with catheter 65 and electrical lead 70 disposed within needle 62 simultaneously. Catheter 65 and electrical lead 70 may be implanted percutaneously within a patient and are not attached to drug pump 68 and neurostimulator 75, respectively. With needle 62 implanted within the patient, catheter 65 and electrical lead 70 may be inserted separately and positioned at a first and a second implant location, respectively. Drug pump 68 and neurostimulator 75 may be implanted subcutaneously within the patient through separate procedures. Catheter 65 and electrical lead 70 may be attached to drug pump 68 and neurostimulator 75, respectively, after being positioned within the patient.

FIG. 4B illustrates needle 62 separate from catheter 65 and electrical lead 70 which are attached to drug pump 68 and neurostimulator 75, respectively. Needle 62 may be withdrawn from a patient after catheter 65 and electrical lead 70 are percutaneously inserted and positioned within the patient. After withdrawing needle 62, catheter 65 and electrical lead 70 may be attached to drug pump 68 and neurostimulator 75, respectively. The patient may receive drug therapy and neurostimulation therapy via catheter 65 and electrical lead 70, respectively.

When implanted in a patient, catheter 65 may be attached to drug pump 68 and electrical lead 70 may be attached to neurostimulator 75 to define a drug therapy system and a neurostimulation system, respectively, that may be used together to treat conditions such as pain, movement disorders, pelvic floor disorders, and gastroparesis. In operation, drug pump 68 delivers dosages of a drug to a first target location within the patient via catheter 65 and neurostimulator 75 generates neurostimulation energy delivered to a second target location within the patient via electrical lead 70. Importantly, catheter 65 and electrical lead 70 may be percutaneously inserted and positioned within the patient by the physician at distinct locations. For example, catheter 65 may be percutaneously inserted in an intrathecal region proximate to the lumbar region of the spine of the patient while electrical lead 70 may be percutanesouly implanted in an epidural region proximate to the thoracic region of the spine of the patient. Alternatively, catheter 65 and lead 70 may be implanted in different epidural regions, e.g., on the left and right side of the spin respectively. In any case, the implantation locations are therapeutically distinct. Drug therapy may be better for some applications and stimulation may be better for others. The invention allows for both drug and stimulation therapy to be facilitated by an implantation procedure that reduces trauma relative to conventional techniques. The stimulation and drug therapy implantation sites may be any of those addressed above, or possibly other sites that can benefit from the teaching of this disclosure.

Figure 5:
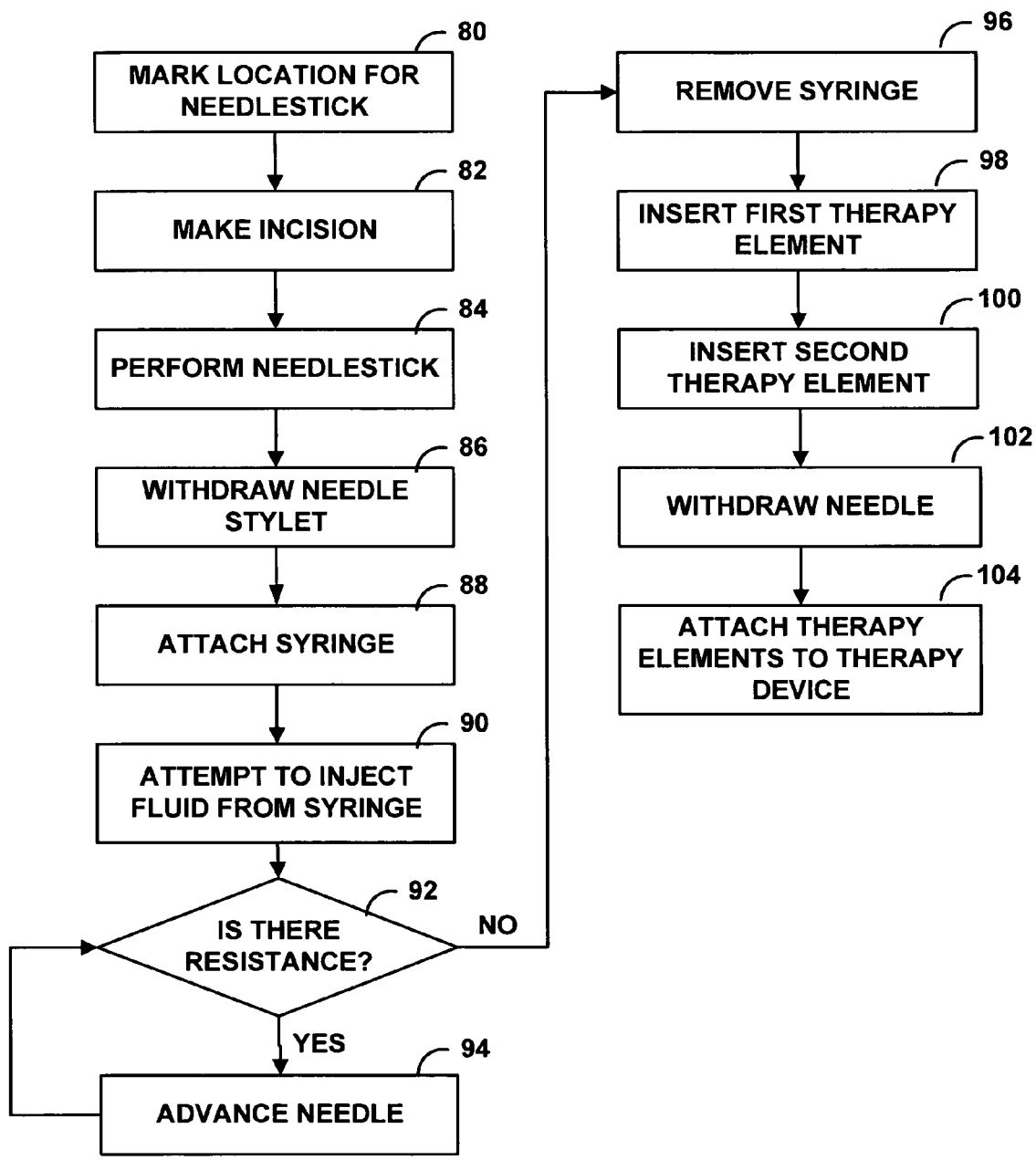
FIG. 5 is a flowchart illustrating an exemplary method for percutaneously implanting two therapy elements using the kit of FIG. 1.

FIG. 5 is a flowchart illustrating an exemplary method for percutaneously implanting first and second therapy elements 6, 8 using needle 4 of kit 2 illustrated in FIG. 1. Initially, a physician may mark a location on the patient for the needlestick (80). The physician makes an incision at the marked location (82) to ease insertion of needle 4 and performs a needlestick at the incision to insert needle 4 (84). Needle 4 may include needle stylet 12 fitted into a lumen defined by cannula 10. The lumen may have a diameter between 14 and 18 gauge to allow cannula 10 to receiver needle stylet 12. Needle stylet 12 may fill the lumen of cannula 10 preventing tissue coring of the patient. In some instances, needle 2 may include a modified Tuohy needle which has an opening that is angled 45 degrees so that an instrument passing through the needle exits at an angle. In some embodiments, the physician may insert needle 4 using a paramedian approach, which provides access to the side of the spinal cord.

After needle 4 has been inserted into the patient, needle stylet 12 is withdrawn (86) and the physician can attach a syringe to cannula 10 (88). The physician may insert needle 4 to access an epidural region proximate to the spine of the patient using a technique referred to as a "loss of resistance technique" to assist in confirming that needle 4 has been properly placed into the epidural region. In particular, the physician may attempt to inject fluid (90), such as air or saline. If the physician experiences substantial resistance when attempting to inject fluid (92), needle 4 is not properly placed in the epidural region and the physician further advances needle 4 to access the epidural region (94). On the other hand, a lack of substantial resistance to fluid from the syringe may indicate that needle 4 has been correctly placed in the epidural region. Once needle 4 has been correctly placed in the epidural region, the syringe may be removed (96) leaving cannula 10 inserted in the patient.

Upon proper placement of needle 4, the physician may optionally insert a guidewire into the epidural region via the lumen defined by needle 4 to clear a path for inserting a therapy element. The guidewire may be maneuvered through the epidural region until it reaches an implant location or target site that is the location where a therapy element will be placed. After the physician has inserted the guidewire to the implant location, the guidewire may be removed and the physician may percutaneously insert first therapy element 6 into the epidural region through the lumen defined by needle 4 (98). In an example embodiment in which first therapy element 6 comprises an electrical lead, the physician may insert first therapy element 6 at a first implant location located in the epidural region proximate to the right lumbar area of the spine of the patient to treat leg pain. Generally, first therapy elements 6 may be positioned at any epidural region proximate to the spine of the patient including the lumbar, thoracic, and cervical regions spine as well as along the mid-line, right side, or left side of the spine of the patient.

Upon inserting first therapy element 6 at a first implant location, the physician may percutaneously insert second therapy element 8 with first therapy element 6 still disposed within needle 4 (100). The physician may maneuver second therapy element 8 to a second implant location. The second implant location may be different that the first implant location such that different therapy can be achieved. However, embodiments in which first and second therapy elements 6, 8 are implanted in a similar location are also envisioned. The invention may provide particular advantages, however, when the electrical leads are placed in different locations. For example, one or more electrodes of the first electrical lead may be positioned at an epidural region proximate to the right lumbar area of the spine of the patient to treat leg pain while one or more electrodes of the second electrical lead may be positioned at an epidural region proximate to the left thoracic area of the spine of the patient to treat lower back pain. In such embodiments, electrodes of the electrical leads may be positioned at any epidural region proximate to the spine of the patient including the lumbar, thoracic, and cervical regions spine as well as along the mid-line, right side, or left side of the spine of the patient.

In other embodiments in which second therapy element 8 comprises a catheter, the physician may percutaneously insert second therapy element 8 to a second implant location located in an intrathecal region proximate to the spine of the patient. The physician may access the intrathecal region by further advancing needle 4. The physician may confirm that the intrathecal region has been accessed when CSF fluid flows into needle 4. After the intrathecal region has been properly accessed, a catheter may be percutaneously inserted while first therapy element 6 is still disposed within needle 4. In general, a catheter may be inserted into an intrathecal region proximate to the spine of the patient while an electrical lead is simultaneously inserted within the patient through needle 4 provided that the intrathecal region can be accessed without withdrawing needle 4.

In any event, first and second therapy elements 6, 8 may be electrical leads, catheters, or an electrical lead and a catheter. In embodiments in which first and second therapy elements 6, 8 comprise electrical leads the invention may provide particular advantages in treating bi-lateral pain by implanting the electrical leads in distinct locations. Additionally, if the electrical leads are separate and not attached to each other, the risk of shorting between the electrical leads reduced. In other embodiments in which first and second therapy elements 6, 8 comprise catheters, the invention may provide similar advantages of allowing drug delivery to different locations. The drugs delivered to the different locations may be the same or different. In accordance with the invention, a single needle and single needlestick can be used for such implantation, and the physician may only needs to access an intrathecal region in such catheter-catheter embodiments. In further embodiments in which first and second therapy elements 6, 8 comprise an electrical lead and a catheter, the invention may provide particular advantages for delivery of drug and stimulation therapy to different locations, possibly in a complementary fashion. Stimulation may be provided to the epidural region with drug therapy to the intrathecal region, possible on a common side of the spine. In general, the invention described herein allows two or more therapy elements to be percutaneously inserted simultaneously through a single needle with one needlestick thereby reducing the risk of trauma to the patient and damage to an already inserted therapy element from an additionally needlestick. Furthermore, the first therapy element may be used as a guide when inserting the second therapy element to further reduce the risk of damaging the already inserted first therapy element.

Once properly implanted, the physician withdraws needles 4 (102) leaving distal ends of first and second therapy elements 6, 8 percutaneously inserted in the patient. The physician then attaches proximal ends of first and second therapy elements 6, 8 to a corresponding therapy device (104). For example, in configurations comprising electrical leads, proximal ends of first and second therapy elements 6, 8 are attached to a neurostimulator. In other configurations comprising catheters, proximal ends of first and second therapy elements are attached to a drug pump or a plurality of drug pumps. In further configurations comprising an electrical lead and a catheter, first and second therapy elements 6, 8 are attached to a neurostimulator and a drug pump, respectively.

Various embodiments of the invention have been described. However, various modifications can be made without departing from the scope of the invention. For example, the various implantation locations described herein may be used for any of the lead-lead, catheter-catheter or lead-catheter embodiments. Moreover, many other therapeutically distinct implantation locations that may benefit from the kit and techniques described herein will become apparent from this disclosure. These and other embodiments are within the scope of the following claims.

The invention claimed is:

1. A method comprising:
inserting a paddle-shaped needle into a patient, the needle defining a lumen sized to receive two or more electrical leads simultaneously and an opening that defines a substantially oblong cross section;
inserting a first electrical lead through the lumen of the needle and out of the opening to position at least one electrode of the first electrical lead at a first implant location in an epidural region proximate to a right lumbar area of the spine of the patient to treat leg pain; and
inserting a second electrical lead through the lumen of the needle and out of the opening to position at least one electrode of the second electrical lead at a second implant location in the epidural region proximate to a left thoracic area of the spine of the patient to treat lower back pain.

2. The method of claim 1, wherein the needle includes a cannula and a needle stylet, wherein the cannula defines the lumen and the needle stylet is sized to substantially fill the lumen to avoid coring of tissue of the patient when the needle stylet is inserted in the cannula and the needle is inserted into the patient.

3. The method of claim 2, wherein inserting the needle includes inserting the needle stylet and the needle cannula and withdrawing the needle stylet from the lumen.

4. The method of claim 2, further comprising attaching a syringe to the cannula and injecting fluid into the first implant location via the syringe to evaluate a position of the needle based on resistance of the fluid from the syringe, advancing the needle when resistance of the fluid is substantial, and removing the syringe when resistance of the fluid is not substantial.

5. The method of claim 1, wherein distal ends of the first and the second electrical leads include one or more electrodes electrically coupled to proximal ends of the first and second electrical leads via one or more conductors that extend along lead bodies of the leads.

6. The method of claim 5, further comprising attaching the proximal ends of the first and the second electrical leads to a neurostimulation device.

7. The method of claim 1, wherein inserting the first electrical lead and inserting the second electrical lead occur at different times.

8. The method of claim 1, further comprising inserting a guidewire through the lumen of the needle to clear a path to one of the first and second implant locations prior to inserting the electrical leads through the lumen.

9. The method of claim 1, further comprising withdrawing the needle and attaching at least one of the first and second electrical leads to a neurostimulation device.

10. The method of claim 1, wherein the opening is angled at approximately 45 degrees so that the first and second electrical leads passing through the paddle-shaped needle exit the paddle-shaped needle at an angle of approximately 45 degrees.

* * * * *